United States Patent [19]

Jamieson

[11] 4,323,057

[45] Apr. 6, 1982

[54] SELF RETAINING UTERINE ELEVATOR

[76] Inventor: David J. Jamieson, 1908 Coffee Rd., Modesto, Calif. 95355

[21] Appl. No.: 153,725

[22] Filed: May 27, 1980

[51] Int. Cl.³ ............................................... A61B 1/32
[52] U.S. Cl. ..................................................... 128/17
[58] Field of Search ............................. 128/17, 345, 20

[56] References Cited

U.S. PATENT DOCUMENTS

| | | | |
|---|---|---|---|
| 2,844,144 | 7/1958 | Massey | 128/17 X |
| 3,320,948 | 5/1967 | Martin | 128/17 |
| 3,789,829 | 2/1974 | Hasson | 128/17 |
| 3,835,843 | 9/1974 | Karman | 128/17 |

*Primary Examiner*—John D. Yasko
*Attorney, Agent, or Firm*—Harvey B. Jacobson

[57] ABSTRACT

A generally conventional speculum including first and second elongated transversely arcuate blades opening toward each other and defining a longitudinal housing therebetween as provided. Mounting structure pivotally connects base ends of the blades for relative swinging of the free blade ends toward and away from each other and enables adjustable lateral shifting of the axis of relative pivoting of the blades toward and away from one of the blades. The mounting structure is operative to adjustably limit swinging of the free blade ends toward each other and an elongated rod is disposed between the blades and extends through the housing with a first end of the rod cradled in the base end of the other blade for longitudinal shifting of the rod relative to the other blade with clamp structure provided for releasably rigidly anchoring the rod in adjusted longitudinal shifted position. The free end of the rod is inclined away from the free end of the other blade toward the free end of the aforementioned one blade when the blades are generally parallel and an abutment is carried by and shiftable along the rod and may be releasably retained in adjusted position therealong. An elongated handle is supported from the base end of the aforementioned one blade and extends generally at right angles relative thereto with the handle projecting substantially directly away from the other blade.

9 Claims, 9 Drawing Figures

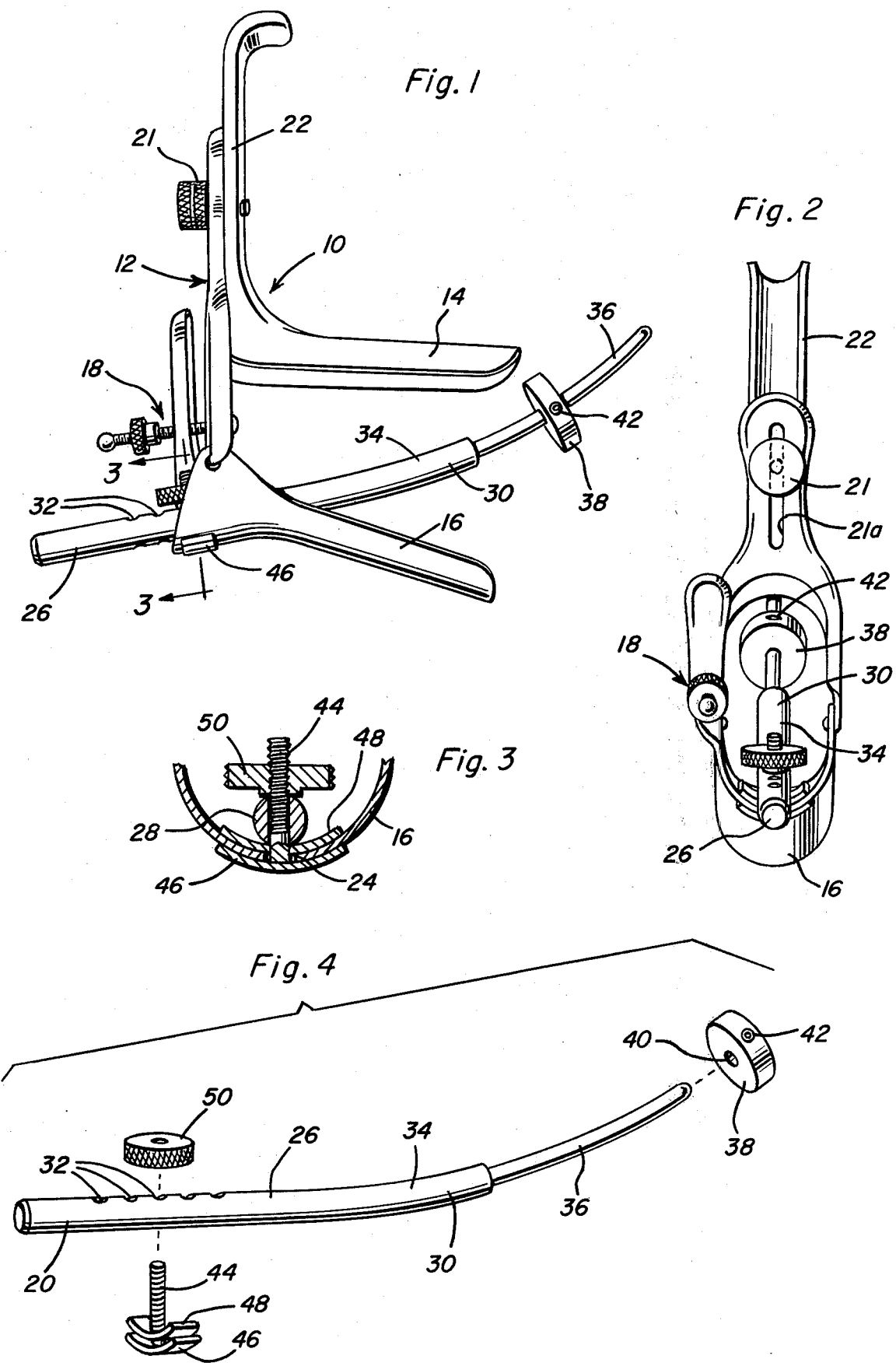

SELF RETAINING UTERINE ELEVATOR

BACKGROUND OF THE INVENTION

In various surgical procedures (notably tubal ligations) it is desirable to elevate the female uterus against the abdominal wall. However, there exists no instrument which may be so simply utilized for this purpose and at the same time retain itself in place. Examples of previously known instruments including some of the general structural and operational features of the instant invention are disclosed in U.S. Pat. Nos. 2,482,622, 2,858,826 and 3,320,948.

BRIEF DESCRIPTION OF THE INVENTION

The uterine elevator of the instant invention has been specifically designed to enable a patient's uterus to be elevated against the abdominal wall and to enable the instrument to be manipulated as desired through the surgical drapes from above the latter.

The instrument is generally in the form of a Graves vaginal speculum, but has been modified in a manner to be utilized somewhat differently and to effect elevation of a patient's uterus during a tubal ligation. The instrument further may be utilized during an abdominal hysterectomy for the purpose of defining a cutting guide in developing the vaginal cuff.

The main object of this invention is to provide a surgical tool which may be effectively utilized by a surgeon or one of the surgeon's assistants to effect elevation of a female uterus toward the abdominal wall during a tubal ligation for easy access of the Fallopian tubes through a small (mini) incision of the abdominal wall overlying the uterus.

Another object of this invention is to provide a surgical tool in accordance with the preceding object and constructed in a manner whereby the tool may be manipulated through surgical drapes from above the latter.

Still another important object of this invention is to provide a surgical tool which will enable the patient's legs to be outstretched, rather than being supported in stirrups during a tubal ligation.

A further object of this invention is to provide a surgical instrument which may be utilized effectively to define a cutting guide in developing the vaginal cuff in the performance of an abdominal hysterectomy.

A final object of this invention to be specifically enumerated herein is to provide a surgical tool which will comform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a side elevational view of the instrument of the instant invention;

FIG. 2 is a back elevational view of the instrument as seen from the left side of FIG. 1.;

FIG. 3 is a fragmentary enlarged transverse vertical sectional view taken substantially upon the place indicated by the section line 3—3 of FIG. 1;

FIG. 4 is an exploded perspective view of the attachment component portion of the instrument which may be utilized to adapt a substantially conventional Graves vaginal speculum in accordance with the instant invention;

DETAILED DESCRIPTION OF THE INVENTION

Figure 5:
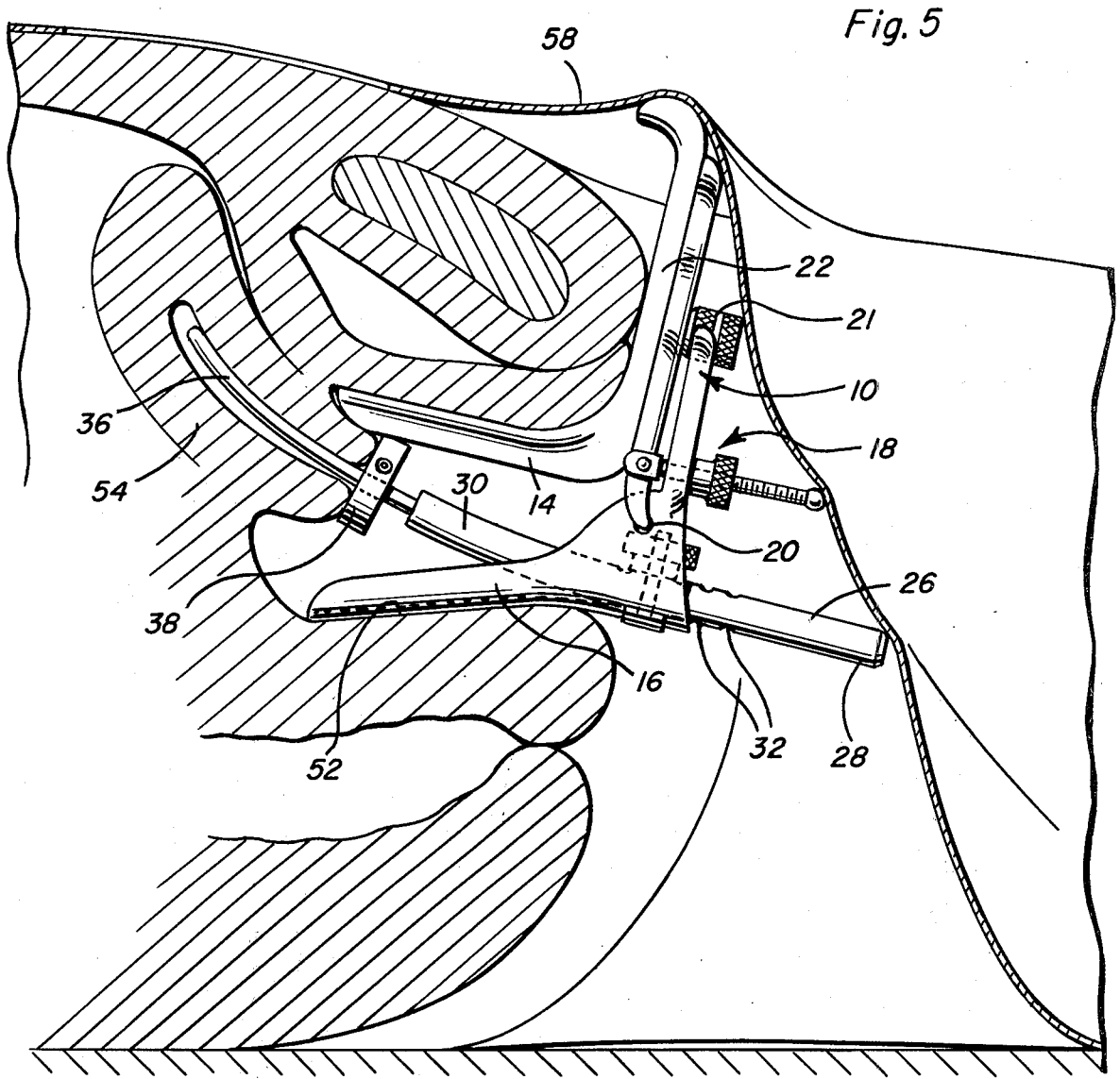
FIG. 5 is a vertical sectional view illustrating the instrument in its use position relative to the female anatomy.
Figure 6:
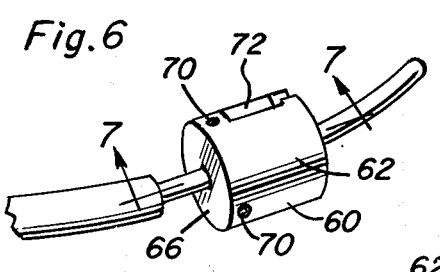
FIG. 6 is a fragmentary perspective view of a cutting guide attachment for the instruction positioned on the shaft portion of the accessory thereof in lieu of the disc-shaped aubtment illustrated in FIG. 4.
Figure 7:
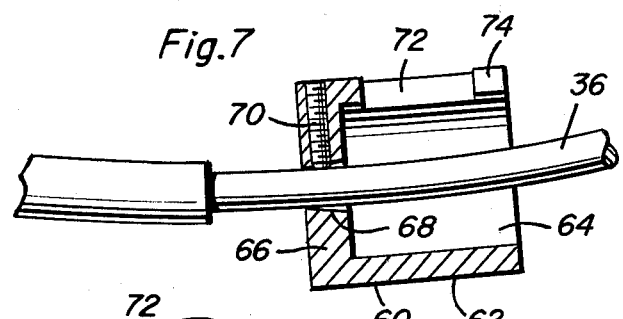
FIG. 7 is an enlarged fragmentary vertical sectional view taken substantially upon the plane indicated by the section line 7—7 of FIG. 6.
Figure 8:
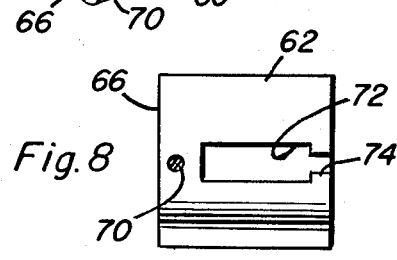
FIG. 8 is a side elevational view of the cutting guide defining cuff.
Figure 9:
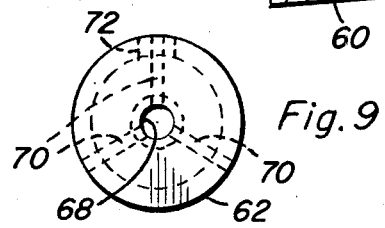
FIG. 9 is a rear elevational view of the cutting guide defining cuff.

Referring now more specifically to the drawings, the numeral 10 generally designates the instrument of the instant invention. The instrument 10 is in the form of a substantially conventional large size Graves vaginal speculum 12 including a pair of elongated transversely arcuate blades 14 and 16 defining an open ended elongated housing. A mounting structure referred to in general by the reference numeral 18 is operatively connected between one pair of corresponding ends of the blades 14 and 16 and defines a pivot axis 20 therebetween about which the blades 14 and 16 may be swung to move the second pair of ends of the blades 14 and 16 remote from the mounting structure 18 toward and away from each other. The mounting structure 18 includes adjustment means 21 whereby the pivot axis 20 may be laterally shifted toward and away from one of the blades 14. Also, the base end of the blade 14 includes an elongated handle 22 supported therefrom and disposed at generally right angles to the blade 14. The handle 22 extends away from the blade 14 in a direction extending away from the blade 16.

The foregoing comprises a description of a conventional Graves vaginal speculum and it is to be noted that the large size Graves vaginal speculum is utilized to construct the instrument of the instant invention.

In modifying the large size Graves vaginal speculum in accordance with the present invention, the base end of the blade 16 includes a small bore 24 and the blades 14 and 16 are shortened from a 5-inch length to a 4-inch length. Further, it will be noted, from FIG. 5 of the drawings, that the speculum is inverted in position relative to its usual position in the vagina.

The instrument 10 additionally includes a substantially straight mounting shaft 26 including base and free ends 28 and 30. The base end 28 includes longitudinally spaced diametric bores 32 formed therethrough and free end 30 of the shaft 26 is angulated aproximately 10° as at 34 and includes a diametrically reduced terminal end 36 having a radius of curvature of substantially 14 cm. A cylindrical abutment disc 38 is provided and has a central bore 40 formed therein whereby the abutment disc 38 may be slidably received on the terminal end 36, the abutment disc 38 including a radial set screw 42 therefor releasably securing the disc 38 in adjusted position on the terminal end 36.

A fastening bolt 44 is provided and includes a partial cylindrical head 46. Also, a partial cylindrical and centrally apertured washer 48 is disposed on the bolt 44. The base end 28 of the shaft 26 is cradled within the base end of the blade 16 and the bolt 44 is inserted into the bore 24 with the head and washer 48 opposing the outer and inner sides of the portion of the blade 16 through which the bore 24 is formed. Then, the shaft 26 is cradled in the base end of the blade 16 with the bolt 44 received through one of the bores 32 and a knurled thumb nut 50 is tightened on the free end of the bolt 44 remote from the head 46. In this manner, the shaft 26 is rigidly anchored in adjusted position relative to the base end of the blade 16. It will be noted that inasmuch as the shaft 26 is cradled in the slightly angulated base end of the blade 16, the shaft 26 is inclined away from the free end of the blade 16.

In operation, the instrument 10, independent of the components 26-50, is initially inserted and opened within the vagina 52 in the manner illustrated in FIG. 5 of the drawings. Then, the uterine fundus is sounded for depth and the abutment disc 38 is accordingly positioned on the terminal end 36 in order that the terminal end 36 will not perforate the uterus. The shaft 26 is then attached to the blade 16 with the bolt 44 being received through bore 34 which is determined will position the shaft 26 to best place the uterus 54 in the desired elevated position and the nut 50 is securely tightened.

It will be noted that by placing the speculum in an inverted position, the handle 22 extends substantially vertically upwardly and thus may be manipulated by the surgeon or one of the surgeon's assistants through the drape 58. Further, inasmuch as manipulative access to the instrument 10 may be gained through the drape 58 from above, the patient's legs may be stretched out rather than supported in stirrups. Also, it will be noted that the blades 14 and 16 may be adjusted so as to be 30° divergent toward their free ends thus enabling the instrument to retain itself in position within the vagina 52 and can be further anchored in the vagina by sliding blades 14 and 16 apart further longitudinally using knurled thumb nut 21 and slot 21a.

With attention now invited more specifically to FIGS. 6-9 of the drawings, when an abdominal hysterectomy is being performed, the abutment disc 38 may be removed and replaced by a cutting guide cup referred to in general by the reference numeral 60. The cup 60 includes a cylindrical body 62 open at one end 64 and closed at the other end by an end wall 66. The end wall 66 has a truncated cone-shaped inwardly flaring bore 68 formed therethrough and three radial set screws 70 are supported on the end wall 66 and may thus be utilized to secure the cup 60 in adjusted canted positions on the terminal end 36. The cylindrical side wall 62 includes a longitudinal slot 72 formed therein opening endwise outwise outwardly through the open end 64 of the cup 60 and the entrance end of the slot 72 is reduced in width as at 74. When the cup 60 is properly positioned on the terminal end 36, it may be utilized as a cutting guide in developing the vagina cuff during abdominal hysterectomy procedures. The slot 72 provides a means whereby the uterine cervix can be grasped by a suitable holding instrument to steady it during the intended use of the instrument.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A speculum for use in inverted position and for manually elevating a female uterus toward the abdominal wall, said speculum including first and second elongated transversely arcuate upper and lower blades opening toward each other and defining a longitudinal open ended housing therebetween, mounting structure connected between the first corresponding ends of said blades relatively pivotally joining said blades for swinging of the second corresponding ends thereof toward and away from each other and adjustable lateral shifting of the axis of relative pivoting of said blades toward and away from one of said blades, said mounting structure including means operative to adjustably limit swinging of said second ends toward each other, an elongated rod disposed between said blades, extending through said housing and having a first base end cradled in the first end of the other blade, said first end of said rod being longitudinally shiftable relative to the other blade first end, clamp means releasably rigidly anchoring said first rod end in adjusted longitudinally shifted position relative to said other blade, the second end of said rod being inclined away from the second end of said other blade and toward the second end of said one blade when said blades are generally parallel and a cervix engaging abutment carried by and shiftable along said second end of said rod, and retaining means operative to releasably retain said abutment in adjusted position on said rod, said second end of said one blade having one end of an elongated handle supported therefrom and disposed at generally right angles relative thereto with the other end of said handle projecting substantially directly away from said other blade.

2. The combination of claim 1 wherein said abutment comprising a substantially cylindrical and centrally apertured disc-shaped body.

3. The combination of claim 1 wherein said abutment includes a cup-shaped body having a generally cylindrical side wall portion and closed at one end by an end wall having a central aperture formed therethrough, said rod being slidably received through said aperture, said cup opening toward said second end of said rod.

4. The combination of claim 3 wherein said aperture is frustoconical in configuration and said retaining means includes a plurality of generally radial set screws threadedly supported from said abutment and spaced about the center axis of said aperture and engageable with said rod along a circumferential zone thereof axially spaced from the minor diameter end of said aperture.

5. The combination of claim 4 wherein one longitudinally extending cylindrical wall portion of said body includes a longitudinal slot formed therein opening through the open end of said body.

6. A speculum function performing apparatus for use in inverted position and for manually elevating a female uterus toward the abdominal wall, said apparatus including body structure defining an elongated housing having first and second ends and including opposite anterior and poterior longitudinal sides and being adjustably transversely expandable for varying the spacing between said longitudinal sides, an elongated rod extending longitudinally through said housing and including first and second ends corresponding to said first and second ends of said housing, the first end of said rod being supported from the inner side of the first end of said posterior longitudinal side, the second end of said rod being inclined toward the second end of said anterior longitudinal side and a cervix engaging abutment carried by, slidable along and releasably securably in adjusted position on the second end of said rod, said first end of said anterior side including a generally right angulated handle supported therefrom projecting away from said posterior longitudinal side.

7. The combination of claim 6 including mounting means mounting said rod from said posterior longitudinal side and operative to rigidly anchor said one end of said rod relative to said posterior longitudinal side in adjusted longitudinally shifted positions relative thereto.

8. The combination of claim 6 wherein said body structure includes adjustment means operatively connected between said anterior and posterior longitudinal sides for adjustably laterally positioning said sides toward and away from each other, said adjustment means including means operative to adjustably variably cant said anterior and posterior longitudinal sides relative to each other about a transverse axis.

9. The combination of claim 6 wherein said abutment comprising a substantially cylindrical and centrally apertured disc-shaped body.

* * * * *